(12) United States Patent
Sonnergren et al.

(10) Patent No.: US 6,906,017 B1
(45) Date of Patent: Jun. 14, 2005

(54) BATH PRODUCT AND METHOD OF USE

(76) Inventors: Borie Pak Sonnergren, P.O. Box 4103, Alexandra, VA (US) 22303-4103; Ban Pak, P.O. Box 4103, Alexandra, VA (US) 22303-4103

( * ) Notice: Subject to any disclaimer, the term of this patent is extended or adjusted under 35 U.S.C. 154(b) by 0 days.

(21) Appl. No.: 10/936,652

(22) Filed: Sep. 9, 2004

(51) Int. Cl.⁷ .............................. A61K 7/00; A01N 59/20
(52) U.S. Cl. ..................... 510/130; 510/131; 424/70.1; 424/400; 424/401; 424/725; 424/736; 424/747; 514/886; 514/887; 514/906; 383/127
(58) Field of Search .................................. 510/130, 131; 424/70.1, 400, 401, 725, 736, 747; 514/886, 887, 906; 383/127

(56) References Cited

U.S. PATENT DOCUMENTS

| | | |
|---|---|---|
| 4,659,495 A | 4/1987 | Figliola |
| 5,958,462 A | 9/1999 | McLean |
| 6,180,115 B1 | 1/2001 | Conrard et al. |
| 6,475,513 B1 | 11/2002 | Yamada |
| 6,581,220 B2 | 6/2003 | Yekutiely |
| 2002/0081341 A1 | 6/2002 | Sott |

OTHER PUBLICATIONS

Web page from www.kalyx.com/catalog/eoplai.htm dated May 28, 2004.

*Primary Examiner*—Necholus Ogden
(74) *Attorney, Agent, or Firm*—Richard C. Litman

(57) ABSTRACT

The bath product employs halite and a mixture of herbs and spices packed in water permeable bath bags to condition bath water and emit fragrances. The bath product includes five water permeable bags contained in an outer carrying bag. Four of the five water permeable bags contain the mixture and one contains halite. The mixture includes ground lemongrass, wrinkled skin lime, wrinkled skin lime leaves, holy basil, *Zingiber cassumunar* Roxb., and mint.

9 Claims, 2 Drawing Sheets

BATH PRODUCT AND METHOD OF USE

BACKGROUND OF THE INVENTION

1. Field of the Invention

The present invention relates to bath products, and more particularly, to a bath product employing halite and a mixture of herbs and spices packed in water permeable bath bags to condition bath water and emit fragrances.

2. Description of the Related Art

Aromatherapy is the use of selected fragrant substances to affect mood and promote health. One type of aromatherapy involves mixing aromatic substances with bath water. Bathing with aromatic substances is known to provide many positive benefits, including soothing and relaxing sore muscles, alleviating postpartum aches, exfoliating skin, and relieving dry skin, as well as affecting mood. However, a specific aromatic substance typically does not affect every person in the same manner. While one aromatic substance may provide some or many benefits to one individual, it may not be beneficial to another individual. Often an individual may try a number of different aromatic substances before finding a suitably beneficial one. Additionally, some aromatic substances are not well suited for use in a bath, or may require a thorough cleaning of the bathtub after use.

Thus, a need exists for an aromatherapy bath product that is beneficial to its users, that can be easily added to a bath in a measured amount, and that allows for easy clean up.

U.S. Patent Publication No. 2002/0081341, published Jun. 27, 2002, describes a method, apparatus and system for customizing essential oil formulations. U.S. Pat. No. 4,659,495, issued Apr. 21, 1987 to V. N. Figliola, describes a bath product for treating bath water that includes a water permeable bag containing powdered moisturizing beads.

U.S. Pat. No. 5,958,462, issued Sep. 28, 1999 to L. McLean, describes therapeutic bath salts for use in aromatherapy. U.S. Pat. No. 6,180,115, issued Jan. 30, 2001 to L. J. Conrard et al., describes a mineral bath kit that includes a water permeable bag containing mineral chips.

U.S. Pat. No. 6,475,513 issued Nov. 5, 2002 to K. Yamada, describes a skin care pouch containing carbide aggregations. U.S. Pat. No. 6,581,220, issued Jun. 24, 2003 to D. Yekutiely, describes a method and apparatus for aromatherapy in a shower.

The herb *Zingiber cassumunar* Roxburgh (*Zingiber cassumunar* Roxb.), a relative of ginger (*Zingiber officinale*, Roscoe), is an herb native to India and Southeast Asia. According to the web site The essential oil called Plai oil in Thailand is extracted from the rhizomes of the plant and is used in aromatherapy as a massage oil, either alone or in combination with other essential oils, for its anti-inflammatory and analgesic effects, according to a web page published on the World Wide Web by the Kalyx.com site at kalyx.com/catalog/eoplai.htm, at least as of May 28, 2004. However, to the best of Applicant's knowledge, *Zingiber cassumunar* Roxb. has not been used in combination with the other herbs of the present composition, nor in a bath product.

None of the above inventions and patents, taken either singly or in combination, is seen to describe the instant invention as claimed. Thus, a bath product solving the aforementioned problems is desired.

SUMMARY OF THE INVENTION

The bath product employs halite and a mixture of herbs and spices packed in water permeable bags to condition bath water and emit fragrances. In a preferred configuration, the bath product includes five water permeable bags contained in an outer carrying bag. Four of the five water permeable bags contain the mixture and one bag contains halite. In one embodiment, the mixture includes at least ground lemongrass, wrinkled skin lime, wrinkled skin lime leaves, holy basil, *Zingiber cassumunar* Roxb., and mint. Alternatively, the mixture may include ground lemongrass, wrinkled skin lime, wrinkled skin lime leaves, holy basil, *Zingiber cassumunar* Roxb., sweet basil, field basil, and mint.

When the water permeable bags are placed in bath water, the mixture releases fragrances that are calming to the bather, and the water is conditioned to soothe and relax muscles, facilitate breathing, as well as to exfoliate skin and relieve dry skin. The conditioned water is also beneficial for relieving eczema, psoriasis, postpartum aches, and alleviating the symptoms associated with sinus infection.

Accordingly, it is a principal object of the invention to provide a bath product that releases fragrances and conditions water when placed in a bath.

It is another object of the invention to provide a bath product that releases fragrances and conditions water when used with a steam bath, a facial steaming machine, and in a sauna.

It is another object of the invention to provide a bath product that is calming to an individual bathing in water conditioned with the bath product for aromatherapy.

It is a further object of the invention to provide a bath product that soothes and relaxes the muscles of an individual bathing in water conditioned with the bath product for aromatherapy.

Still another object of the invention is to provide a bath product that exfoliates skin and relieves dry skin, eczema, and psoriasis for an individual bathing in water conditioned with the bath product for aromatherapy.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
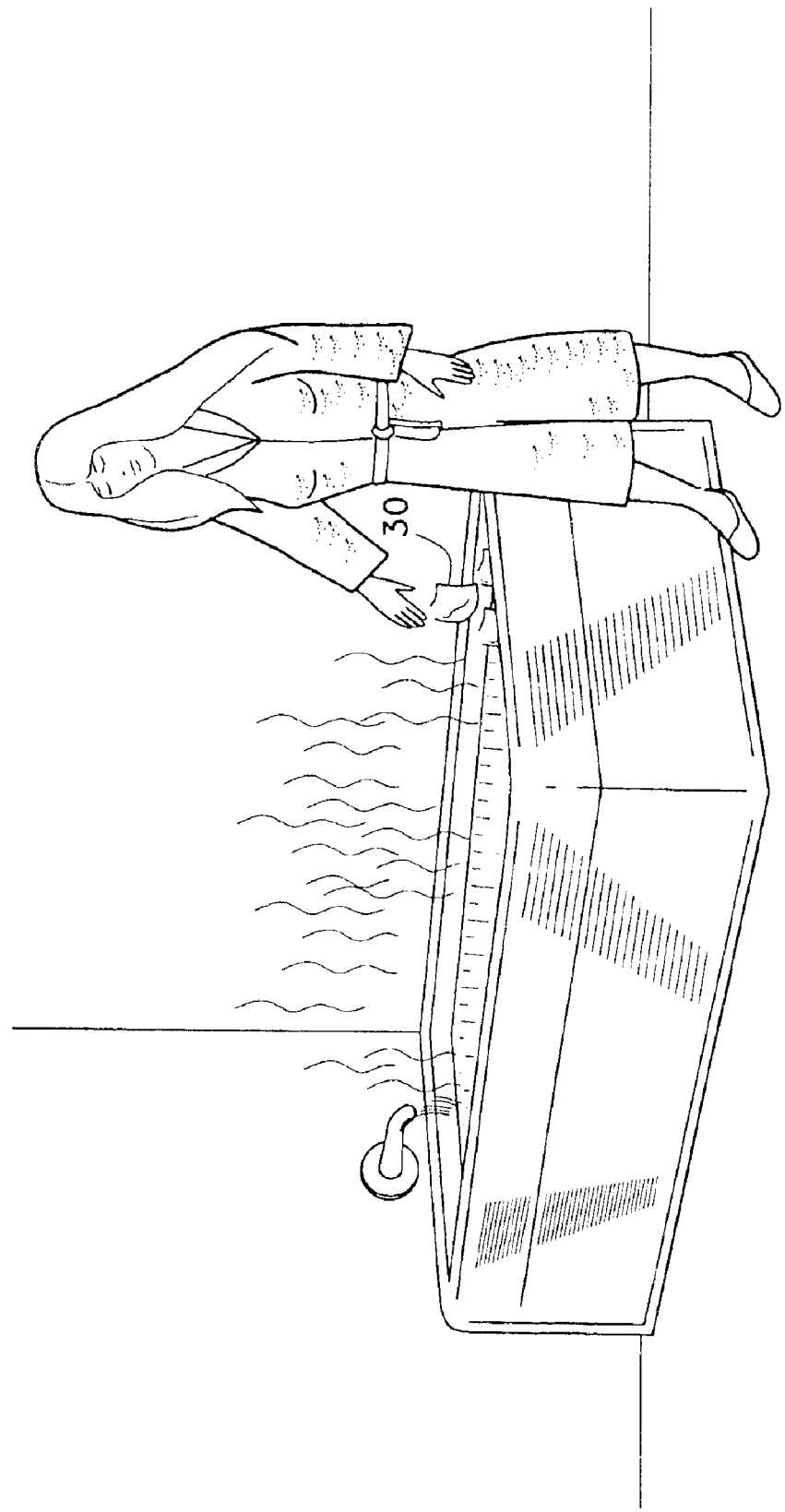
FIG. 1 is an environmental, perspective view of a bath product according to the present invention as used by a person about to take a bath.

The present invention is a bath product for aromatherapy, designated generally as 10 in the drawings, and a method of use of the product. The bath product 10 employs a quantity of halite and a mixture of herbs and spices packed in water permeable bath bags to condition bath water and emit fragrances.

Figure 2:
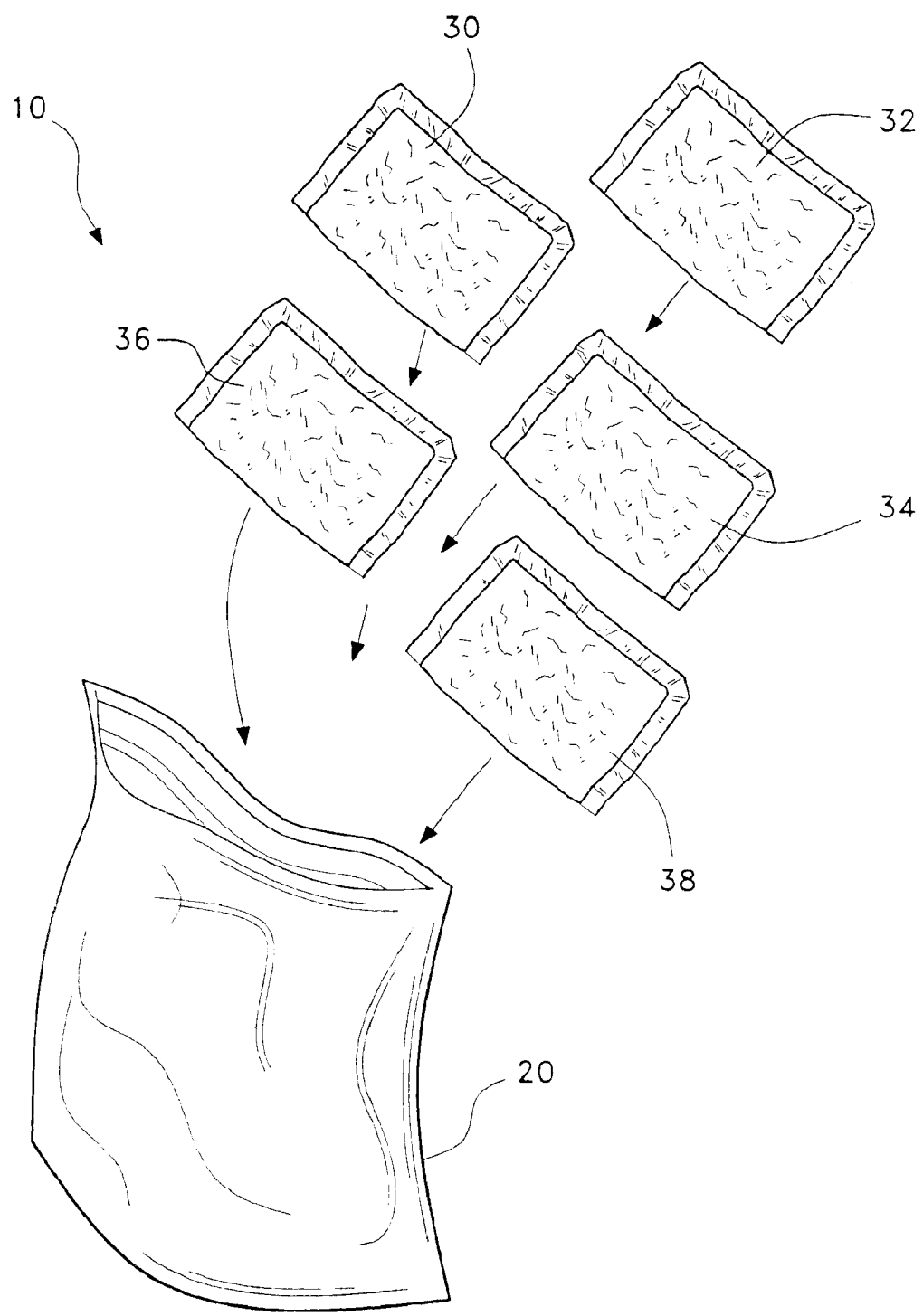
FIG. 2 is an exploded view of a bath product for aromatherapy.

Referring to FIGS. 1 and 2, the bath product 10 may include five water permeable bags 30, 32, 34, 36 and 38 contained in an outer carrying bag 20. In one embodiment, four 30, 32, 34 and 36 of the five water permeable bags contain a mixture of ground lemongrass, wrinkled skin lime, wrinkled skin lime leaves, sweet basil, field basil, holy basil, *Zingiber cassumunar* Roxb., and mint. Alternatively, however, the four water permeable bags 30, 32, 34 and 36 may contain ground lemongrass, wrinkled skin lime, wrinkled skin lime leaves, holy basil, *Zingiber cassumunar* Roxb., sweet basil, field basil, and mint. The fifth water permeable bag 38 contains halite.

While both rock salt and rock sea salt are a form of halite or crystalline sodium chloride, it is commonly believed that rock sea salt contains trace amounts of minerals, which would be especially beneficial in bath products. However, both rock salt and rock sea salt may be used in the present invention. Thus, the term halite, as used herein, can refer to either rock salt or rock sea salt. The term rock salt refers to salt that is mined from solid layers in the ground. The term rock sea-salt refers to salt produced by evaporation from seawater.

In one embodiment, the mixture includes by weight about 14.2% ground lemongrass, about 14.2% ground wrinkled skin lime, about 14.2% ground wrinkled skin lime leaves, about 14.2% ground holy basil, about 14.2% ground *Zingiber cassumunar* Roxb., and about 7.1% ground mint.

In an alternative embodiment, the mixture includes by weight about 10.14% ground lemongrass, about 10.14% ground wrinkled skin lime, about 10.14% ground wrinkled skin lime leaves, about 10.14% ground sweet basil, about 10.14% field basil, about 10.14% ground holy basil, about 29.02% ground *Zingiber cassumunar* Roxb., and about 10.14% ground mint.

Each of the water permeable bags 30, 32, 34, 36 and 38 is constructed of a single rectangular sheet of one hundred percent woven cotton that is about 7 5/8"" long by about five inches wide. The sheet is folded in half width-wise, with the mating edges sealed to form a bath bag about 3 13/16" long by about five inches wide. Prior to sealing the mating edges, three tablespoons of either the mixture or halite is inserted between the two halves of the folded sheet. Thus, each of the bags containing the mixture 30, 32, 34 and 36 contains about three tablespoons of the mixture, and the bag 38 containing halite contains about three tablespoons of halite. It will be understood that the number of bags of the mixture of herbs will vary, depending upon the size of the bags, the above dimensions being representative of a preferred packaging only, and not limiting.

The outer carrying bag 20 is a vacuum-packed, plastic bag dimensioned to hold the five water permeable bags 30, 32, 34, 36 and 38, which are packed therein.

When the water permeable bags 30, 32, 34, 36 and 38 are placed in bath water, as shown in FIG. 1, the mixture releases fragrances that are calming to the bather and the water is conditioned to sooth and relax the muscles of the bather, facilitate breathing, as well as to exfoliate skin and relieve dry skin. Consequently, the bath product 10 is especially useful after exercise. Additionally, the conditioned water is beneficial for relieving eczema, psoriasis, postpartum aches, and alleviating the symptoms associated with sinus infection.

The bath product 10 also can be used with either a steam bath, a facial steaming machine, or in a sauna by placing one of the packets containing the mixture 30, 32, 34 and 36 into the water supply of the steamer.

In addition to its health benefits, the bath product 10 also is useful for cleansing. Thus, the bath product is useful for individuals sensitive to soaps as an alternative means of cleaning.

In an alternative embodiment, the bath product 10 may include one water permeable bag containing halite and only one water permeable bag containing a mixture of at least ground lemongrass, wrinkled skin lime, wrinkled skin lime leaves, holy basil, *Zingiber cassumunar* Roxb., and mint in the amounts described above. This embodiment would be useful for a bath prepared for a baby, or for soaking the hands, feet, or arms.

The bath product 10 does not leave a ring in a bathtub and therefore allows for easy clean up. Similarly, the bath product 10 does not leave any residual on an individual.

It is possible to use each bath bag 30, 32, 34, 36 and 38 and its contents more than once.

It is to be understood that the present invention is not limited to the embodiment described above, but encompasses any and all embodiments within the scope of the following claims.

We claim:

1. A bath product, comprising:

halite; and a mixture of lemongrass, wrinkled skin lime, wrinkled skin lime leaves, holy basil, *Zingiber cassumunar* Roxburgh, and mint.

2. The bath product according to claim 1, wherein said mixture comprises, by weight:

about 14.2% lemongrass;

about 14.2% wrinkled skin lime;

about 14.2% wrinkled skin lime leaves;

about 14.2% holy basil;

about 14.2% *Zingiber cassumunar* Roxburgh; and about 7.1% mint.

3. The bath product according to claim 1, further including sweet basil.

4. The bath product according to claim 1, further including field basil.

5. The bath product according to claim 1, further comprising a first, second, third, fourth and fifth water permeable bag, said mixture being contained within each of said first, second, third and fourth water permeable bags, said halite being contained within said fifth water permeable bag.

6. The bath product according to claim 3, further comprising an outer carrying bag, said first, second, third, fourth and fifth water permeable bags being contained within said outer carrying bag for transport and storage.

7. The bath product of claim 1, wherein said halite is rock sea salt.

8. The bath product of claim 1, wherein said halite is rock salt.

9. A method of using a bath product, comprising the steps of:

packaging an effective amount of halite in a first water permeable bag;

packaging a mixture of effective amounts of lemongrass, wrinkled skin lime, wrinkled skin lime leaves, holy basil, *Zingiber cassumunar* Roxburgh, and mint into at least one second water permeable bag; and placing said first and second water permeable bags into a bathtub containing bath water.

* * * * *